United States Patent [19]

Injev

[11] Patent Number: 5,634,912
[45] Date of Patent: Jun. 3, 1997

[54] INFUSION SLEEVE

[75] Inventor: Valentine P. Injev, Irvine, Calif.

[73] Assignee: Alcon Laboratories, Inc., Fort Worth, Tex.

[21] Appl. No.: 599,771

[22] Filed: Feb. 12, 1996

[51] Int. Cl.$^6$ .................................................. A61M 5/00
[52] U.S. Cl. ............................................. 604/264; 604/22
[58] Field of Search .................. 604/264, 22, 27–30, 604/35, 282, 240

[56] References Cited

U.S. PATENT DOCUMENTS

| | | |
|---|---|---|
| 4,681,561 | 7/1987 | Hood et al. . |
| 4,808,154 | 2/1989 | Freeman . |
| 5,084,009 | 1/1992 | Mackool . |
| 5,188,589 | 2/1993 | Wypych et al. . |
| 5,282,786 | 2/1994 | Ureche . |
| 5,286,256 | 2/1994 | Mackool . |
| 5,354,265 | 10/1994 | Mackool . |

*Primary Examiner*—John D. Yasko
*Attorney, Agent, or Firm*—Jeffrey S. Schira

[57] ABSTRACT

An infusion sleeve having a two-piece body. The first piece is conical in shape and is attached to the handpiece by conventional methods. The distal end of the first piece contains a series of annular grooves. The second piece is tubular in shape and contains an annular rim or lip on the proximal end that interlocks within the annular grooves on the first piece.

4 Claims, 5 Drawing Sheets

5,634,912

INFUSION SLEEVE

BACKGROUND OF THE INVENTION

The present invention relates generally to endoscopic surgical equipment and more specifically to infusion sleeves used in phacoemulsification.

Phacoemulsification involves emulsifying the natural lens in situ using an ultrasonically vibrating hollow needle. The emulsified lens is aspirated out of the eye through the hollow needle simultaneously with the infusion of a saline solution. The saline solution is generally infused through the space between the outside of the needle and a thin, flexible sleeve that is held coaxial with the needle. One of the primary benefits of phacoemulsification is that the lens can be removed through a very small incision. With the recent introduction of foldable intraocular lenses, and the ability to insert these replacement lenses through even smaller incisions, the desirable size of the incision through which the phacoemulsification tip and irrigating sleeve must pass is also becoming smaller.

While the desirable phacoemulsification incision size has become smaller, the overall diameter of the cutting tip/sleeve combination has remained relatively constant. As a result, the tip/sleeve combination must be used in a very tight wound. While the elasticity of the eye tissue allows some manipulation of the tip/sleeve within the wound, this tight wound structure holds the sleeve tightly, and prevents the tip from being rotated within the wound. While rotation of the tip is not as important for square cut tips, tips that have been cut on a bevel or that contain a slight bend at the distal end often must be rotated within the eye to take full advantage of the design of the particular tip.

Accordingly, a need continues to exist for an infusion sleeve that permits the cutting tip to be rotated within tight wounds and for a sleeve that reduces excess infusate flow out of the wound, thus allowing for more precise fluidic balance and control.

BRIEF SUMMARY OF THE INVENTION

The present invention improves upon prior art infusion sleeves by providing a sleeve having a two-piece body. The first piece is conical in shape and is attached to the handpiece by conventional methods or can be formed as part of the handpiece. The distal end of the first piece contains a series of annular grooves. The second piece is tubular in shape and contains an annular rim or lip on the proximal end that interlocks within the annular grooves on the first piece. This set of interlocking annular grooves and rim permits the second piece to be rotated about the handpiece and permits the length of the second piece relative to the handpiece to be adjusted.

Accordingly, one objective of the present invention is to provide an infusion sleeve having a two-piece body.

Another objective of the present invention is to provide a rotatable and adjustable infusion sleeve.

Yet another objective of the present invention is to provide an infusion sleeve having a two-piece body, the pieces being connected by a rim on one piece fitting within an annular groove on the other piece.

Still another objective of the present invention is to provide an infusion sleeve that reduces excess fluid flow out of the wound.

These and other advantages and objectives of the present invention will become apparent from the detailed description, drawings and claims that follow.

DETAILED DESCRIPTION OF THE INVENTION

Figure 1:
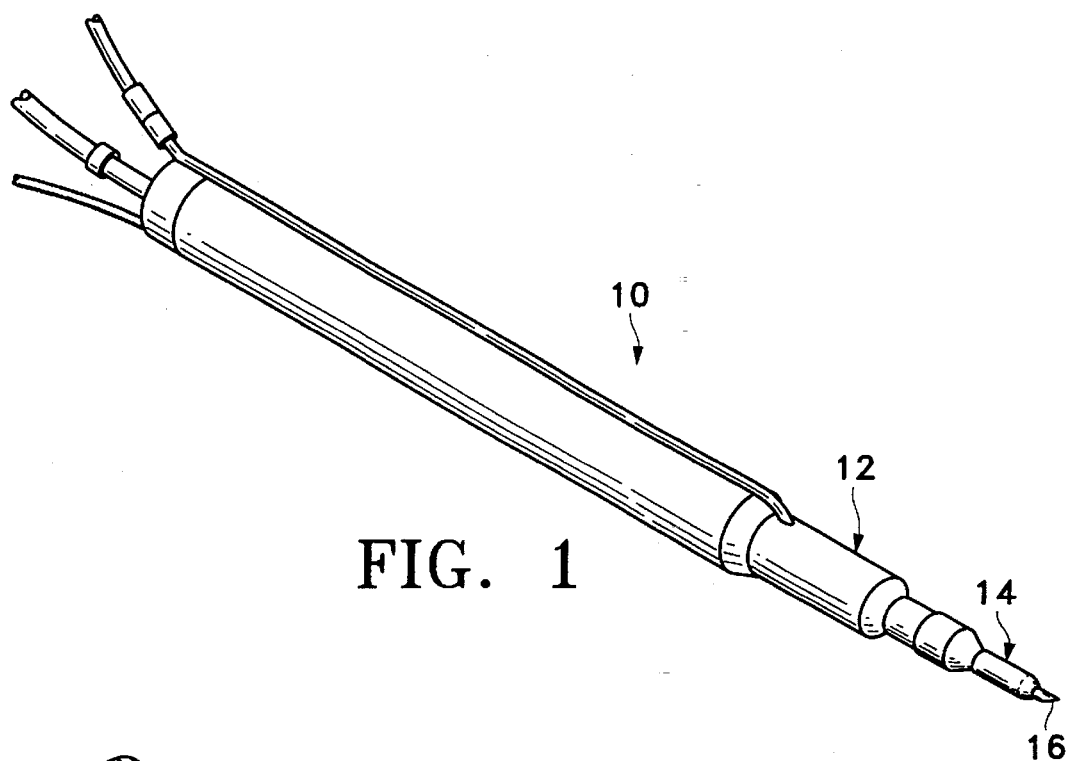
FIG. 1 is a perspective view of a prior art phacoemulsification handpiece.

As can be seen in FIG. 1, prior art phacoemulsification handpiece 10 generally includes handpiece shell 12, infusion sleeve 14 and cutting tip 16 that normally projects a short distance out of sleeve 14. Sleeve 14 normally contains a set of female threads (not shown) that permits sleeve 14 to be screwed onto mating males threads (not shown) on shell 12. Such a construction rigidly attaches sleeve 14 to shell 12.

Figure 2:
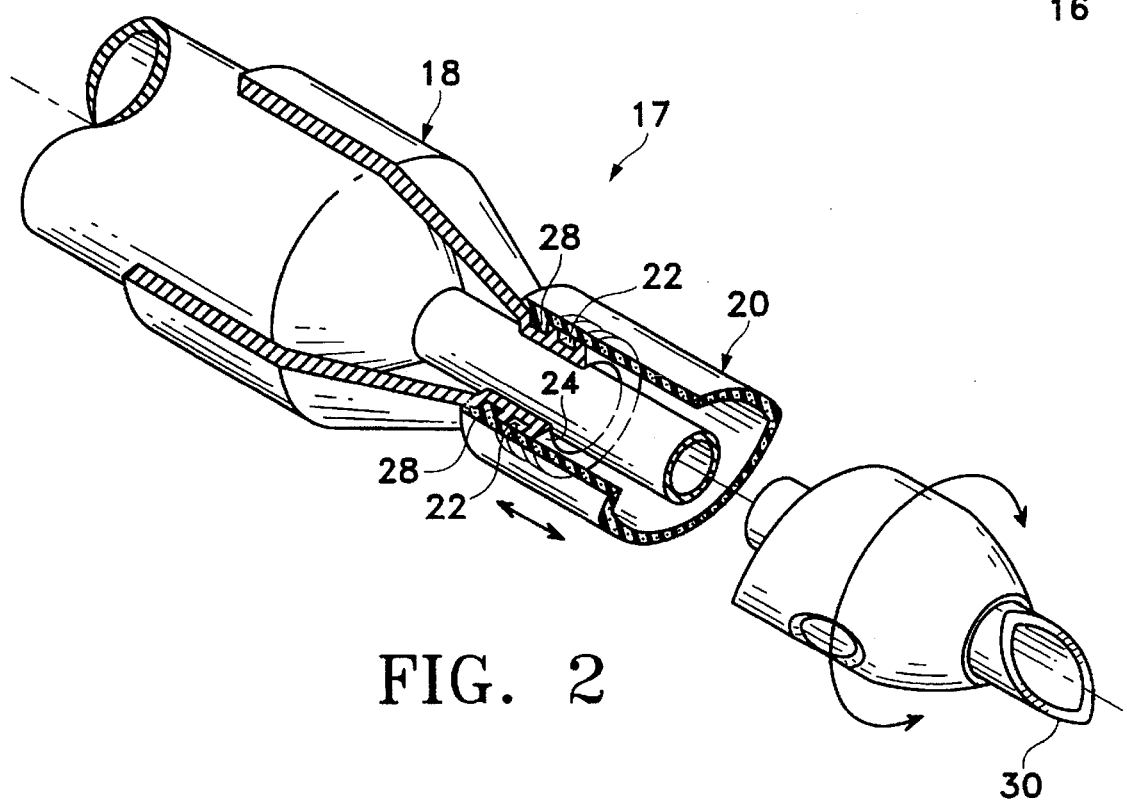
FIG. 2 is an exploded, perspective view of a first embodiment of the present invention, with the handpiece shown in partial cross-section.
Figure 3:
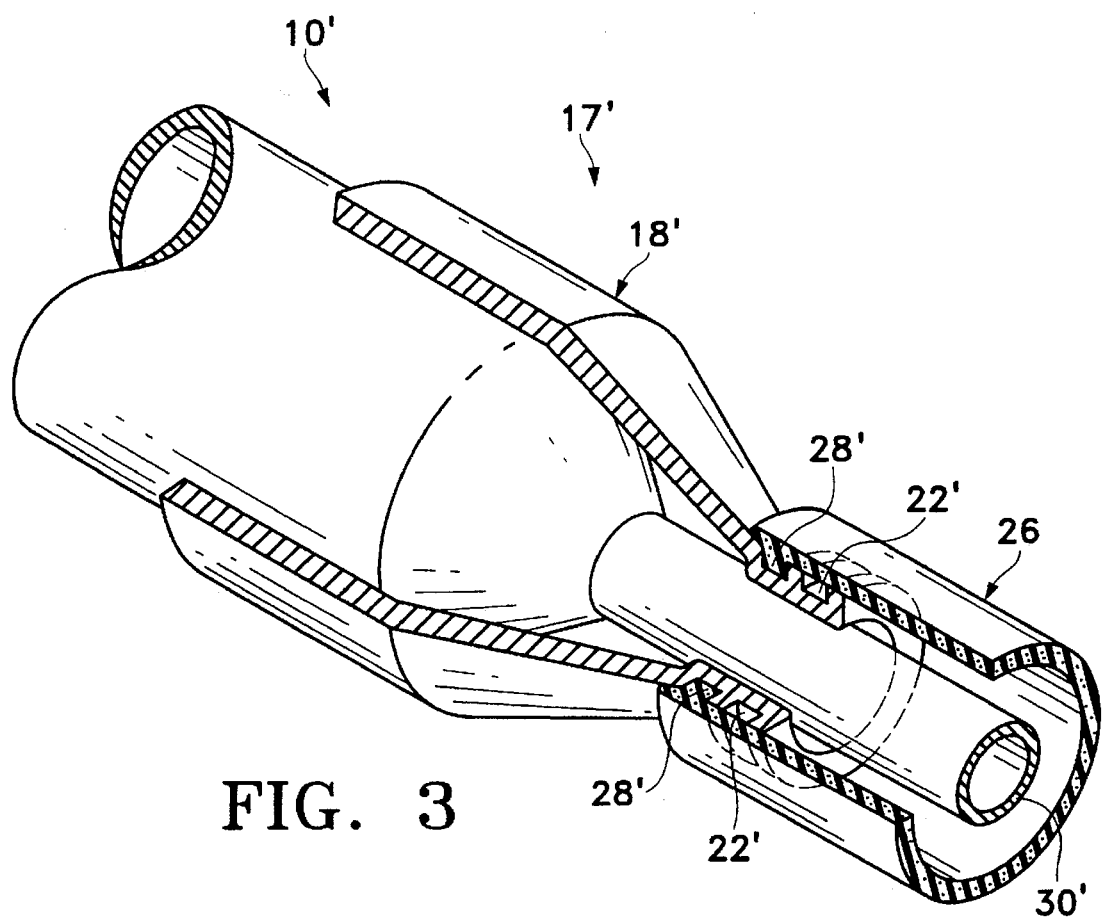
FIG. 3 is an exploded, perspective view of a second embodiment of the present invention, similar to FIG. 2.
Figure 4:
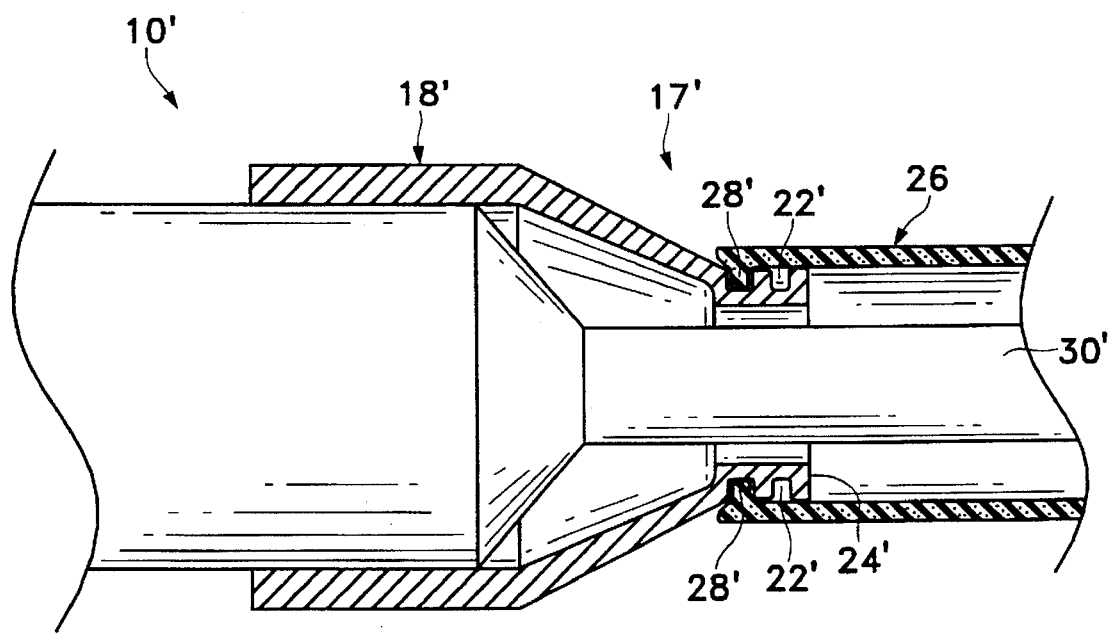
FIG. 4 is a longitudinal cross-section of the second embodiment of the present invention illustrated in FIG. 3
Figure 5:
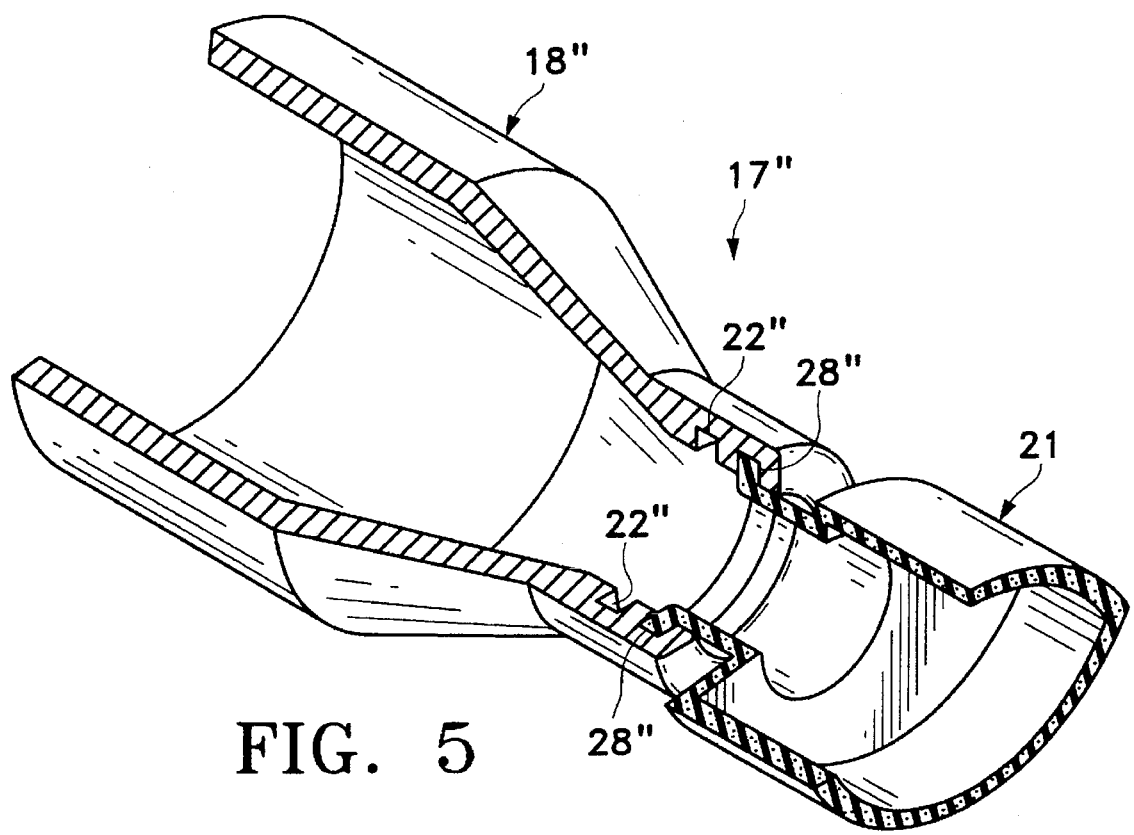
FIG. 5 is a partial cross-section of the third embodiment of the present invention.
Figure 6:
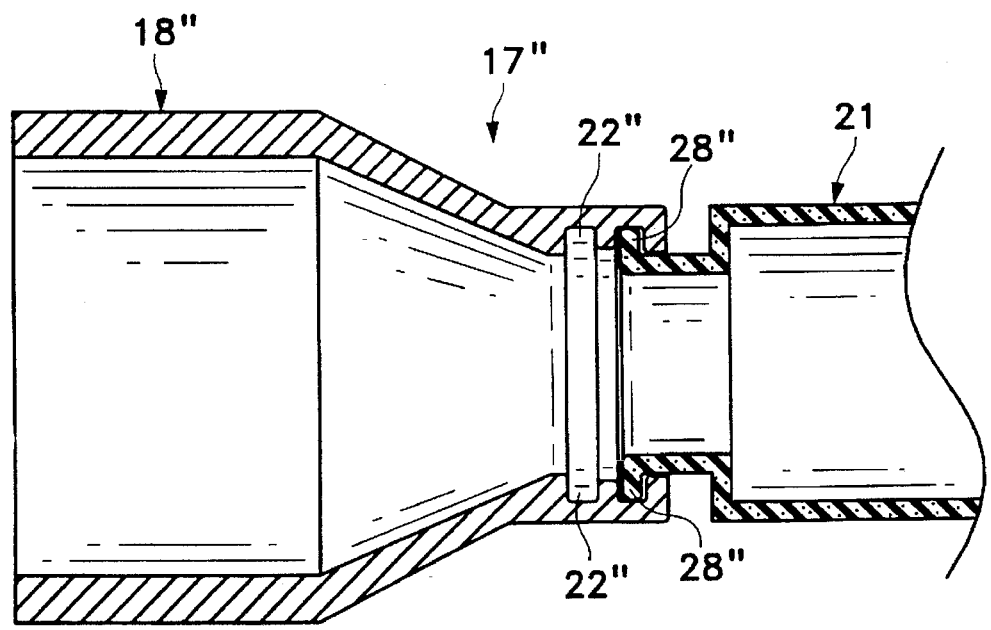
FIG. 6 is a longitudinal cross-section of the third of the present invention illustrated in FIG. 5.
Figure 9:
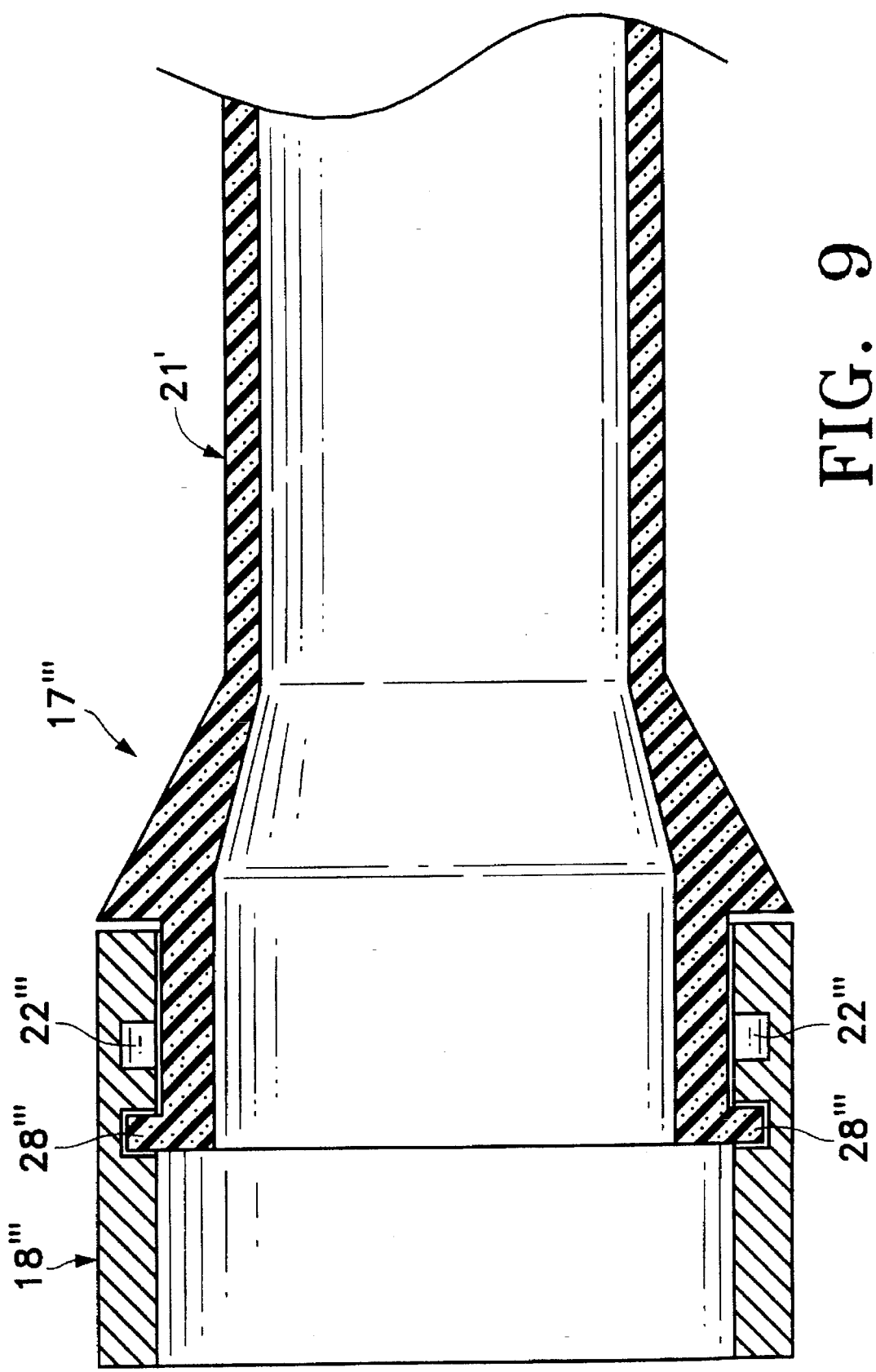
FIG. 9 is a longitudinal cross-section of a fifth embodiment of the present invention similar to the embodiment illustrated in FIG. 6.

As seen in FIG. 2, infusion sleeve 17 of the present invention generally consists of hollow mounting body 18 and rotatable sheath 20. Body 18 may be made of any suitable rigid or flexible material such as titanium, stainless steel, composite materials well-known in the art or silicone rubber. Body 18 is sized and shaped to mount on the distant end of prior art handpiece shell 12 by any suitable means, such as a threaded connection (not shown) or may be formed as a part of shell 12. Body 18 may be generally conical, as illustrated in FIGS. 2–6, or generally tubular, as illustrated in FIG. 9. Body 18 contains at least one and preferably a plurality of annular grooves 22 integrally molded in distal end 24 of body 18 that cooperate with sheath 20 in the manner described below. Grooves 22 and 22' may be molded on the exterior of body 18, as illustrated in FIGS. 2, 3 and 4. Alternatively, grooves 22" or 22'" may be molded on the interior of body 18" or 18'", respectively, as illustrated in FIGS. 5, 6 and 9.

Sheaths 20, 26 and 21 may be generally tubular in shape, as illustrated in FIGS. 2–6, or sheath 21' may be conical, as illustrated in FIG. 9. Sheaths 20, 26, 21 and 21' are preferably formed as a single piece from silicone rubber or other suitable material. Sheaths 20, 21, 21' or 26 may contain ribs or texturing, such as described in U.S. Pat. Nos. 4,808,154 (Freeman) and 5,188,589 (Wypych) or other means to prevent collapse of sheaths 20, 21, 21' and 26, such as those structures described in U.S. Pat. Nos. 5,084,009, 5,286,256, 5,354,265 (Mackool) and 5,282,786 (Ureche), the entire contents of these patents being incorporated herein by reference. In the embodiments illustrated in FIGS. 2 and 5, sheaths 20 and 21 are elliptical in transverse cross-section but, in the embodiment illustrated in FIG. 3, sheath 26 is round in transverse cross-section. Other suitable geometric shapes that best conform to the shape of the wound may also be used for sheaths 20, 21, 21' and 26. By conforming the cross-sectional shape of sheaths 20, 21, 21' and 26 to the shape of the wound, infusate leakage out of the wound may be reduced. By way of example, sheaths 20 and 21 have an outer diameter of the major axis of between 0.07 inches and 0.14 inches, an outer diameter of the minor axis of between 0.04 inches and 0.07 inches, and a wall thickness of between 0.001 inches and 0.01 inches. Sheath 26 has an outer diameter of between 0.04 inches and 0.2 inches, an inner diameter of between 0.02 inches and 0.199 inches and a wall thickness of between 0.001 inches and 0.01 inches. Sheaths 20, 26, 21 and 21' also contain rims or lips 28, 28', 28" and 28''', respectively, which are sized and shaped to nest within grooves 22, 22', 22" and 22''', respectively. This nesting of rims 28, 28', 28" and 28''' within grooves 22, 22', 22" and 28''', together with the flexibility of sheaths 20, 26, 21 and 21', permits sheaths 20, 26, 21 or 21' to rotate relative to body 18, 18', 18" or 18''', respectively. The use of a plurality of grooves 22, 22', 22" and 22''' arranged in series permits 20, 26, 21 and 21' to be lengthen or shortened relative to body 18, 18', 18" or 18''' so that, for example, in the embodiments illustrated in FIGS. 2 and 3, cutting tip 30 or 30' projects the appropriate distance out of sheaths 20 or 26, respectively.

Figure 7:
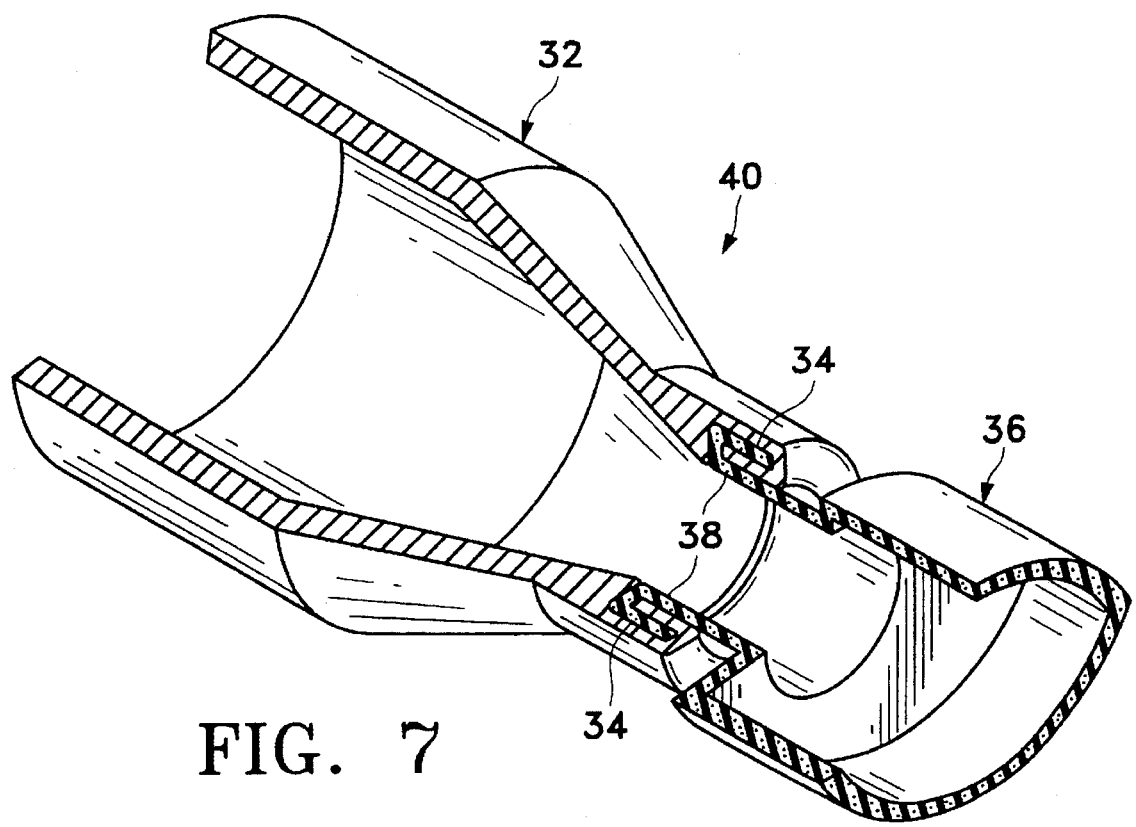
FIG. 7 is a partial cross-section of a fourth embodiment of the present invention.
Figure 8:
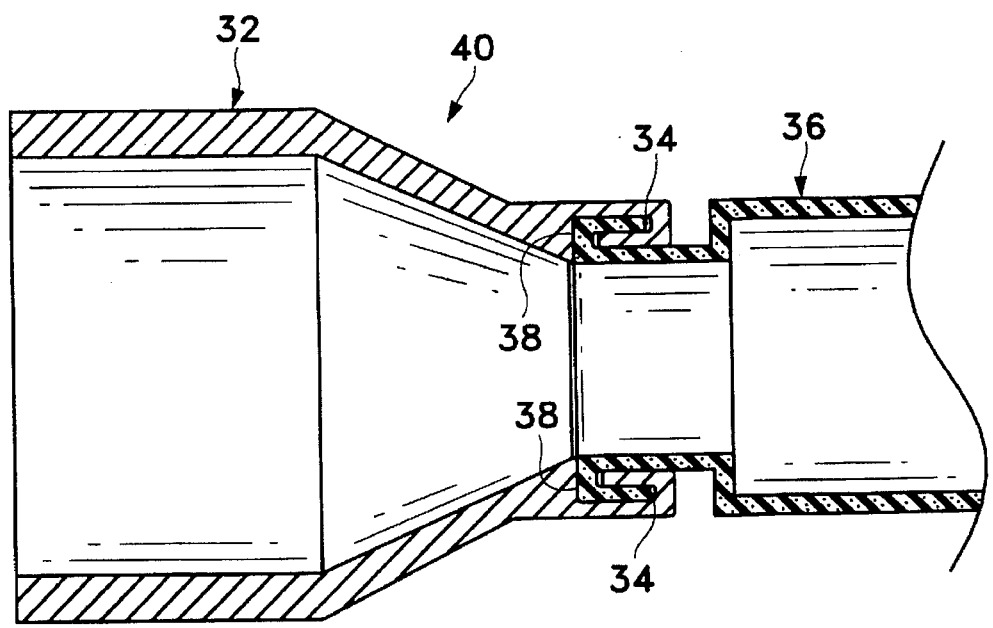
FIG. 8 is a longitudinal cross-section of a fourth embodiment of the present invention illustrated in FIG. 7.

In another embodiment of the present invention 40, illustrated in FIGS. 7 and 8, body 32 does not contain grooves, but uses internal, annular channel 34 that is generally "U"-shaped in cross-section. Sheath 36, which may be round or elliptical in transverse cross-section, contains annular flange 38 that is generally "J"-shaped and nests within channel 34. Such a construction permits rotation of sheath 36 relative to body 32, but restricts longitudinal movement of sheath 36 relative to body 32.

This description is given for purposes of illustration and explanation. It will be apparent to those skilled in the relevant art that modifications may be made to the invention as herein described without departing from its scope or spirit. For example, the invention as illustrated in FIGS. 2–9 may also be used with an irrigation/aspiration handpiece (not shown).

We claim:

1. An infusion sleeve, comprising:
   i) a body having an exterior and at least one annular groove formed on the exterior at a distal end; and
   ii) a sheath having an annular rim on a proximal end the rim sized and shaped to nest within the annular groove on the body.

2. The infusion sleeve of claim 1 wherein the sheath comprises silicone rubber.

3. The infusion sleeve of claim 1 wherein the sheath is elliptical in transverse cross-section.

4. The infusion sleeve of claim 1 wherein the sheath is round in transverse cross-section.

* * * * *